(12) United States Patent
Link et al.

(10) Patent No.: US 12,740,866 B2
(45) Date of Patent: Sep. 22, 2026

(54) PROSTHESES WITH FLEXIBLE SURFACE LAMELLAS

(71) Applicant: WALDEMAR LINK GMBH & CO. KG, Hamburg (DE)

(72) Inventors: Helmut D. Link, Hamburg (DE); Eckhard Bauer, Kiel (DE)

(73) Assignee: WALDEMAR LINK GMBH & CO. KG, Hamburg (DE)

( * ) Notice: Subject to any disclaimer, the term of this patent is extended or adjusted under 35 U.S.C. 154(b) by 533 days.

(21) Appl. No.: 18/248,375

(22) PCT Filed: Oct. 13, 2021

(86) PCT No.: PCT/EP2021/078296
§ 371 (c)(1),
(2) Date: Apr. 7, 2023

(87) PCT Pub. No.: WO2022/079093
PCT Pub. Date: Apr. 21, 2022

(65) Prior Publication Data

US 2024/0033093 A1 Feb. 1, 2024

Related U.S. Application Data

(60) Provisional application No. 63/120,103, filed on Dec. 1, 2020, provisional application No. 63/091,219, filed on Oct. 13, 2020.

(51) Int. Cl.

| | |
|---|---|
| ***A61F 2/30*** | (2006.01) |
| ***A61B 17/72*** | (2006.01) |
| ***A61C 8/00*** | (2006.01) |

(52) U.S. Cl.
CPC ...... *A61F 2/30771* (2013.01); *A61B 17/7283* (2013.01); *A61C 8/0037* (2013.01);
(Continued)

(58) Field of Classification Search
CPC ........ A61F 2/30771; A61F 2002/30151; A61F 2002/30158; A61F 2002/30205;
(Continued)

(56) References Cited

U.S. PATENT DOCUMENTS

| | | | | |
|---|---|---|---|---|
| 8,167,619 B2 * | 5/2012 | Vachtenberg ........ | A61C 8/0033 623/17.17 |
| 2011/0251697 A1 * | 10/2011 | Chung .................. | A61F 2/3662 623/23.15 |

(Continued)

FOREIGN PATENT DOCUMENTS

| | | |
|---|---|---|
| DE | 19705571 A1 | 9/1998 |
| FR | 2549717 A1 | 2/1985 |

(Continued)

OTHER PUBLICATIONS

Communication pursuant to Article 94(3) EPC mailed Mar. 27, 2025, in connection with European Patent Application No. 21794490.9, filed Mar. 29, 2023, 7 pgs.

(Continued)

*Primary Examiner* — Edward Moran
*Assistant Examiner* — Christine L Nelson
(74) *Attorney, Agent, or Firm* — Chiesa Shahinian & Giantomasi PC

(57) ABSTRACT

A prosthesis or implant device for use in joint or bone repair, or restoration of function. The prosthesis or implant device comprises a stem, in which a portion of the stem comprises non-overlapping lamellas around part or all of the circumference of the stem. Each lamella is connected to the external surface of the stem via a bending joint, which permits the space between the rest of the inner surface of the lamella and the external surface of the stem to decrease upon application of a force to the outer surface of the lamella. In addition, methods of treating a subject in need of joint
(Continued)

replacement or bone repair using the prosthesis or implant device.

20 Claims, 12 Drawing Sheets

(52) U.S. Cl.
CPC ................. *A61C 2008/0046* (2013.01); *A61F 2002/30151* (2013.01); *A61F 2002/30158* (2013.01); *A61F 2002/30205* (2013.01); *A61F 2002/30209* (2013.01); *A61F 2002/30224* (2013.01); *A61F 2002/30228* (2013.01); *A61F 2002/30252* (2013.01); *A61F 2002/30827* (2013.01); *A61F 2002/30861* (2013.01)

(58) Field of Classification Search
CPC .. A61F 2002/30209; A61F 2002/30224; A61F 2002/30228; A61F 2002/30252; A61F 2002/30827; A61F 2002/30861; A61C 8/3312–0018; A61C 8/0037; A61C 2008/0046; A61B 17/7283
See application file for complete search history.

(56) References Cited

U.S. PATENT DOCUMENTS

2014/0004481 A1* 1/2014 Spahn .................. A61C 8/0037 433/201.1
2016/0317198 A1 11/2016 Fox
2017/0258557 A1 9/2017 Lee

FOREIGN PATENT DOCUMENTS

FR 2634643 A1 2/1990
FR 2681239 A1 3/1993
FR 2783702 A1 3/2000

OTHER PUBLICATIONS

International Search Report and Written Opinion mailed Jan. 27, 2022, in connection with International Patent Application No. PCT/EP2021/078296, filed Oct. 13, 2021, 16 pgs.

* cited by examiner

PROSTHESES WITH FLEXIBLE SURFACE LAMELLAS

CROSS-REFERENCE TO RELATED APPLICATION(S)

This application is a National Stage under 35 U.S.C. 371 of International Patent Application No. PCT/EP2021/078296, filed Oct. 13, 2021, which claims the benefit of U.S. Provisional Patent Application No. 63/091,219, which was filed on Oct. 13, 2020, and U.S. Provisional Patent Application No. 63/120,103, which was filed on Dec. 1, 2020, the disclosures of all of which are incorporated herein by reference in their entireties.

FIELD OF INVENTION

The invention is associated with the field of orthopedic implants, in particular prostheses and implants for joint replacement, bone repair, and restoration of function.

BACKGROUND OF THE INVENTION

Prostheses are a common tool for repairing joints that have lost full or partial function due to damage, disease, or injury. Surgical implantation of a prosthetic device often involves insertion of a portion of the device, such as a stem, into bone. For instance, in total hip arthroplasty the femoral component comprises a stem that is inserted into the femur, and in knee replacement surgery the tibial component has a stem that extends into the tibia.

One of the main purposes of the stem is to provide stability of the prosthesis within the bone. Consequently, it is critical that the stem can be securely fitted. However, current stem designs are often inflexible and upon insertion can cause damage to the surrounding bone. For instance, stems known in the art are typically made of metal such as cobalt chrome alloy and, as demonstrated in FIGS. 1A-1C, the surface of these stems 1 may be smooth 2, textured 3, or have features such as ridges 4 made of same material as the rest of the stem. As a result, these stems are incompressible, and insertion of these stems into bone can damage the surrounding bone tissue. Such damage may impede osseointegration of the tissue with the stem and ultimately lead to an unstable implant.

Thus, there remains a need in the art for a prosthesis with a stem component that can be inserted into bone without causing damage to the surrounding tissue.

SUMMARY OF INVENTION

In one aspect, the present invention relates to a prosthesis for use in joint or bone repair, the prosthesis comprising a stem. In another aspect, the present invention relates to a dental implant for use in dental repair or restoration of function, the dental implant comprising a stem.

In embodiments of the invention, the stem of the prosthesis or the dental implant has a proximal end, a distal end, and an external surface, in which a portion of the stem comprises two or more non-overlapping lamellas around part or all of the circumference of the stem. Each lamella comprises an outer surface, an inner surface, and a thickness therebetween, in which the inner surface of the lamella faces the external surface of the stem. Each lamella is connected to the external surface of the stem via a bending joint on the inner surface of the lamella at one edge of the lamella or adjacent thereto, in which the rest of the inner surface of the lamella and the external surface of the stem is separated by a space. The bending joint permits the space between the rest of the inner surface of the lamella and the external surface of the stem to decrease upon application of a force to the outer surface of the lamella.

In some embodiments, the stem comprises substantially a shape of a cylinder. The cylinder may be a circular cylinder or an elliptical cylinder.

In some embodiments, the stem comprises a taper between the proximal end and the distal end. In certain embodiments, the stem comprises substantially a shape of a rounded cone or portion thereof. The rounded cone may be a rounded circular cone or a rounded elliptical cone.

In some embodiments, the lamellas are arranged in two or more columns of lamellas in the direction of the proximal end to the distal end of the shaft, and two or more rows of lamellas around the circumference of the shaft. The number of lamellas in each column and each row may be the same, or may not be the same.

In some embodiments, each lamella comprises substantially a shape of a quadrilateral. In certain embodiments, one or more lamellas comprise substantially a shape of a trapezoid, and/or one or more lamellas comprise substantially a shape of a parallelogram.

In some embodiments, each lamella comprises a proximal edge, a distal edge, a left edge, and a right edge. The bending joint may be on the right edge of the lamella or adjacent thereto, or on the left edge of the lamella or adjacent thereto, or on the distal edge of the lamella or adjacent thereto, or on the proximal edge of the lamella or adjacent thereto.

In some embodiments, the bending joint provides on the edge of the lamella, or adjacent thereto, a single continuous connection point between the inner surface of the lamella and the external surface of the stem. Or, the bending joint may provide on the edge of the lamella, or adjacent thereto, two or more connection points between the inner surface of the lamella and the external surface of the stem.

In some embodiments, one or more lamellas comprise a porous coating on the outer surface of the lamellas or a portion thereof.

In some embodiments, the prosthesis of the invention may be a hip replacement prosthesis, a knee replacement prosthesis, or a shoulder replacement prosthesis.

In one aspect, the present invention relates to an intramedullary nail for use in joint or bone repair. The intramedullary nails comprises a shaft having a proximal end, a distal end, and an external surface, in which a portion of the shaft comprises two or more non-overlapping lamellas around part or all of the circumference of the shaft. Each lamella comprises an outer surface, an inner surface, and a thickness therebetween, in which the inner surface of the lamella faces the external surface of the shaft. Each lamella is connected to the external surface of the shaft via a bending joint on the inner surface of the lamella at one edge of the lamella or adjacent thereto, in which the rest of the inner surface of the lamella and the external surface of the shaft is separated by a space. The bending joint permits the space between the rest of the inner surface of the lamella and the external surface of the shaft to decrease upon application of a force to the outer surface of the lamella.

In some embodiments, the shaft comprises substantially a shape of a cylinder. The cylinder may be a circular cylinder or an elliptical cylinder.

In some embodiments, the shaft comprises a taper between the proximal end and the distal end. In certain embodiments, the shaft comprises substantially a shape of a rounded cone or portion thereof. The rounded cone may be a rounded circular cone or a rounded elliptical cone.

In some embodiments, the lamellas are arranged in two or more columns of lamellas in the direction of the proximal end to the distal end of the shaft, and two or more rows of lamellas around the circumference of the shaft. The number of lamellas in each column and each row may be the same, or may not be the same.

In some embodiments, each lamella comprises substantially a shape of a quadrilateral. In certain embodiments, one or more lamellas comprise substantially a shape of a trapezoid, and/or one or more lamellas comprise substantially a shape of a parallelogram.

In some embodiments, each lamella comprises a proximal edge, a distal edge, a left edge, and a right edge. The bending joint may be on the right edge of the lamella or adjacent thereto, or on the left edge of the lamella or adjacent thereto, or on the distal edge of the lamella or adjacent thereto, or on the proximal edge of the lamella or adjacent thereto.

In some embodiments, the bending joint provides on the edge of the lamella, or adjacent thereto, a single continuous connection point between the inner surface of the lamella and the external surface of the shaft. Or, the bending joint may provide on the edge of the lamella, or adjacent thereto, two or more connection points between the inner surface of the lamella and the external surface of the shaft.

In some embodiments, one or more lamellas comprise a porous coating on the outer surface of the lamellas or a portion thereof.

An aspect of the present invention relates to the use of the prosthesis of the invention. Some embodiments are directed to a method of treating a subject in need of joint replacement. The joint replacement may be selected from hip replacement, knee replacement, and shoulder replacement. Some embodiments are directed to a method of treating a subject in need of bone repair. Some embodiments are directed to a method of reducing risk of bone damage caused by implantation of a prosthesis in a subject. Some embodiments are directed to a method of reducing incidence of bone damage caused by implantation of a prosthesis in a subject. Some embodiments are directed to a method of reducing incidence of aseptic implant loosening in a subject. These methods may comprise implanting into the subject the prosthesis of the present invention.

An aspect of the present invention relates to the use of the implant device of the invention. Some embodiments are directed to a method of treating a subject in need of dental repair, the method comprising implanting the dental implant of the present invention. In certain embodiments, the dental implant may support a dental prosthesis such as a crown, bridge, denture, or facial prosthesis, or to act as an orthodontic anchor.

An aspect of the present invention relates to the use of the intramedullary nail of the invention. Some embodiments are directed to a method of treating a subject in need of bone repair. Some embodiments are directed to a method of reducing risk of bone damage caused by implantation of an intramedullary nail in a subject. Some embodiments are directed to a method of reducing incidence of bone damage caused by implantation of an intramedullary nail in a subject. These methods may comprise implanting into the subject the intramedullary nail of the present invention.

BRIEF DESCRIPTION OF THE DRAWING FIGURES

The present disclosure will be further explained with reference to the attached drawing figures, wherein like structures are referred to by like numerals throughout the several views. The drawing figures shown are not necessarily to scale, with emphasis instead generally being placed upon illustrating the principles of the present disclosure, and some features may be exaggerated to show details of particular components. In addition, any measurements, specifications, and the like shown in the drawing figures, or described below, are intended to be illustrative, and not restrictive. Therefore, specific structural and functional details disclosed herein are not to be interpreted as limiting, but merely as a representative basis for teaching one skilled in the art to variously employ the prostheses and implant devices and methods of their use.

FIG. 1A shows a stem having a smooth surface, FIG. 1B shows a stem having a textured surface, and FIG. 1C shows a stem having a surface that comprises ridges.

FIG. 2A shows a view of the stem, and FIG. 2B shows a perspective cut-away view of the stem.

FIG. 5A shows a perspective cut-away view of the proximal end of the stem, and FIG. 5B shows a perspective view of the lamellas.

FIG. 6A shows a perspective cut-away view of the stem, and FIG. 6B shows a perspective view of the lamellas.

Figure 7:
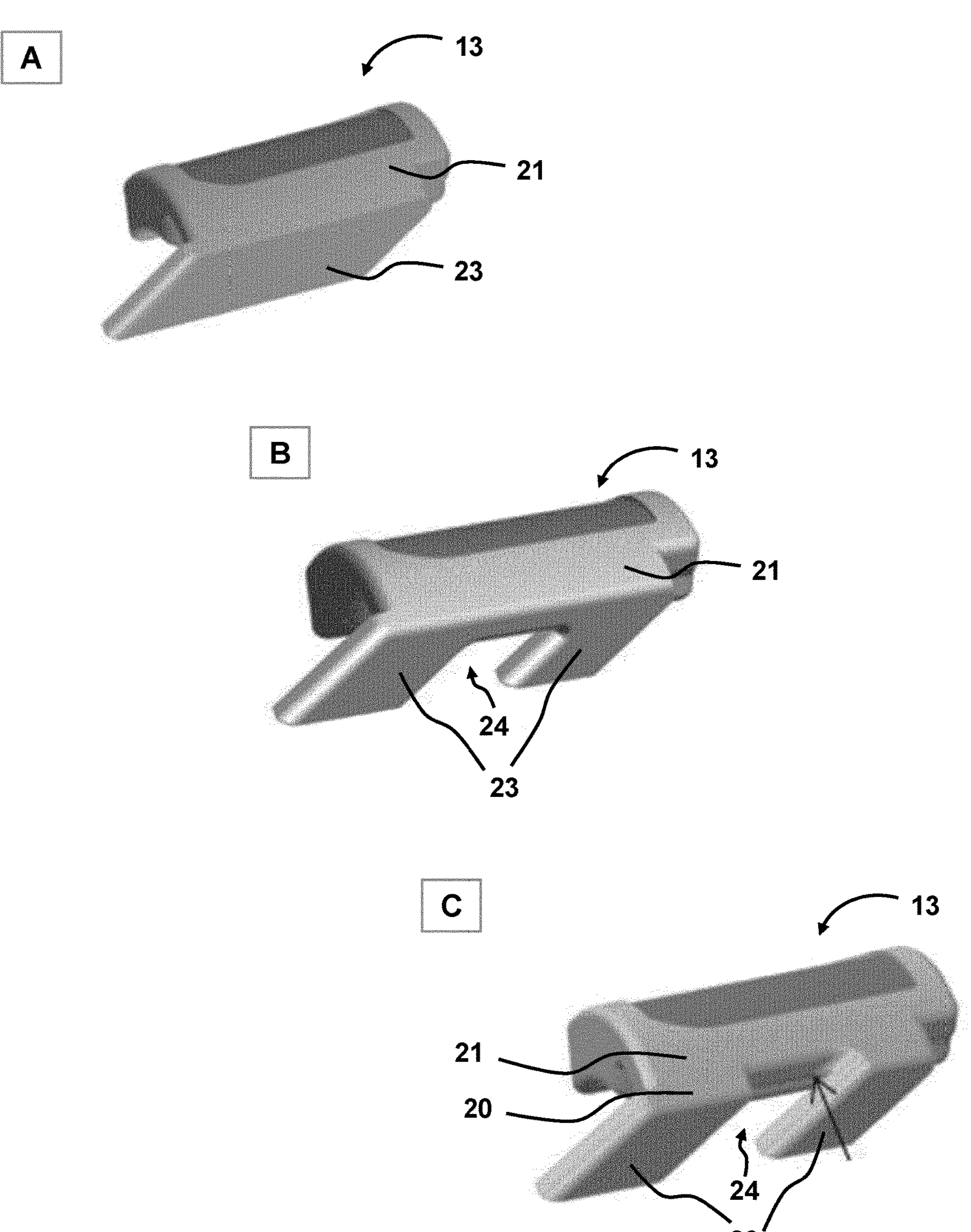

FIGS. 7A-7C show how the inner surface of the lamella connects to the external surface of the stem at the bending joint, according to embodiments of the invention. FIG. 7A shows a perspective view of the bending joint comprising a single continuous connection point between the lamella and the external surface of the stem; FIG. 7B shows a perspective view of the bending joint having a disconnected portion in the connection point between the lamella and the external surface of the stem; and FIG. 7C shows a perspective view of the bending joint having a disconnected portion in the connection point between the lamella and the external surface of the stem, in which the disconnected portion extends into the thickness of the bending joint.

Figure 8:
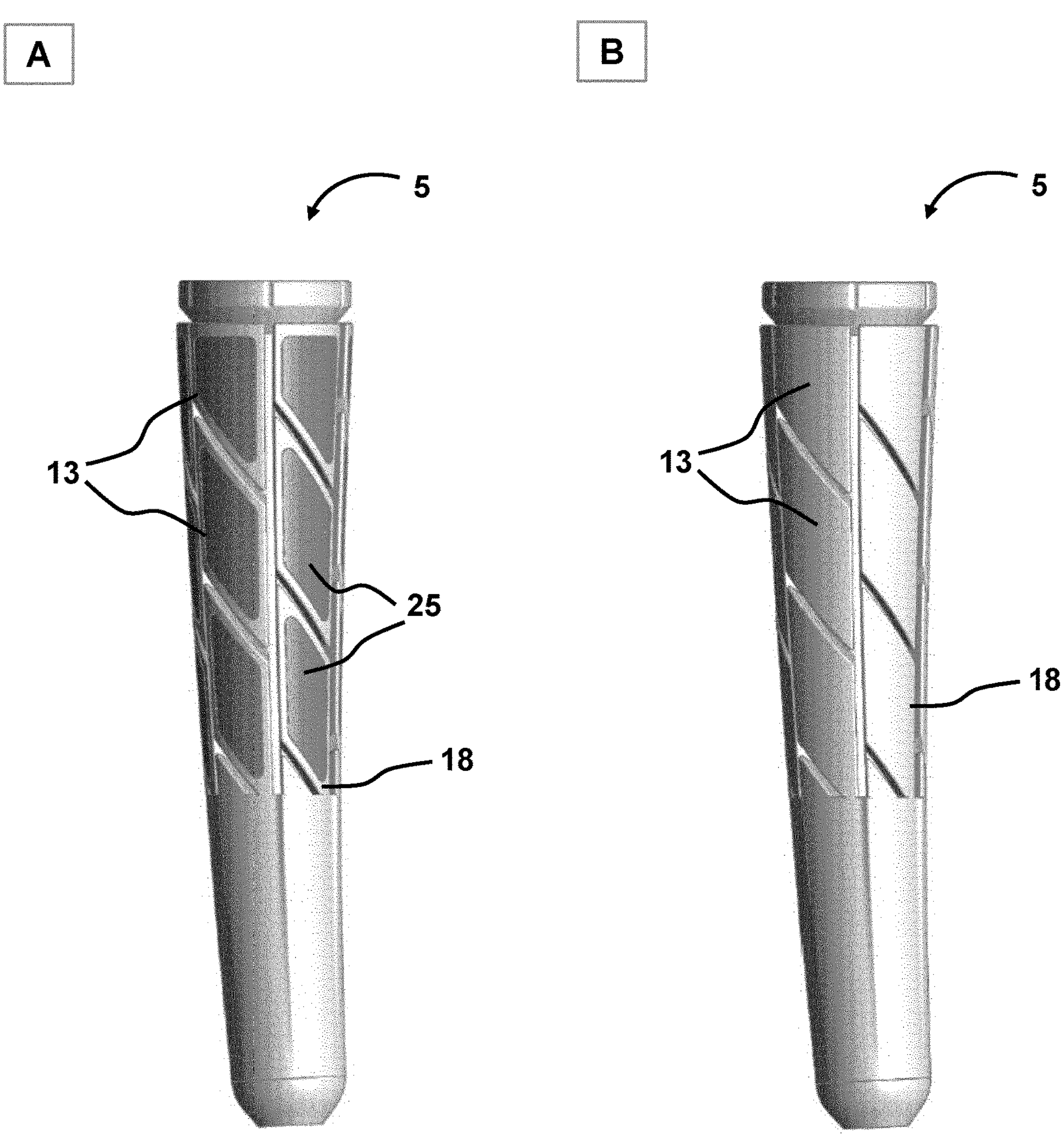

FIGS. 8A and 8B show the stem according to embodiments of the invention, in which FIG. 8A shows a view of a stem having lamellas with a surface feature on their outer surface, and FIG. 8B shows a view of a stem having lamellas without a surface feature on their outer surface.

Figure 9:
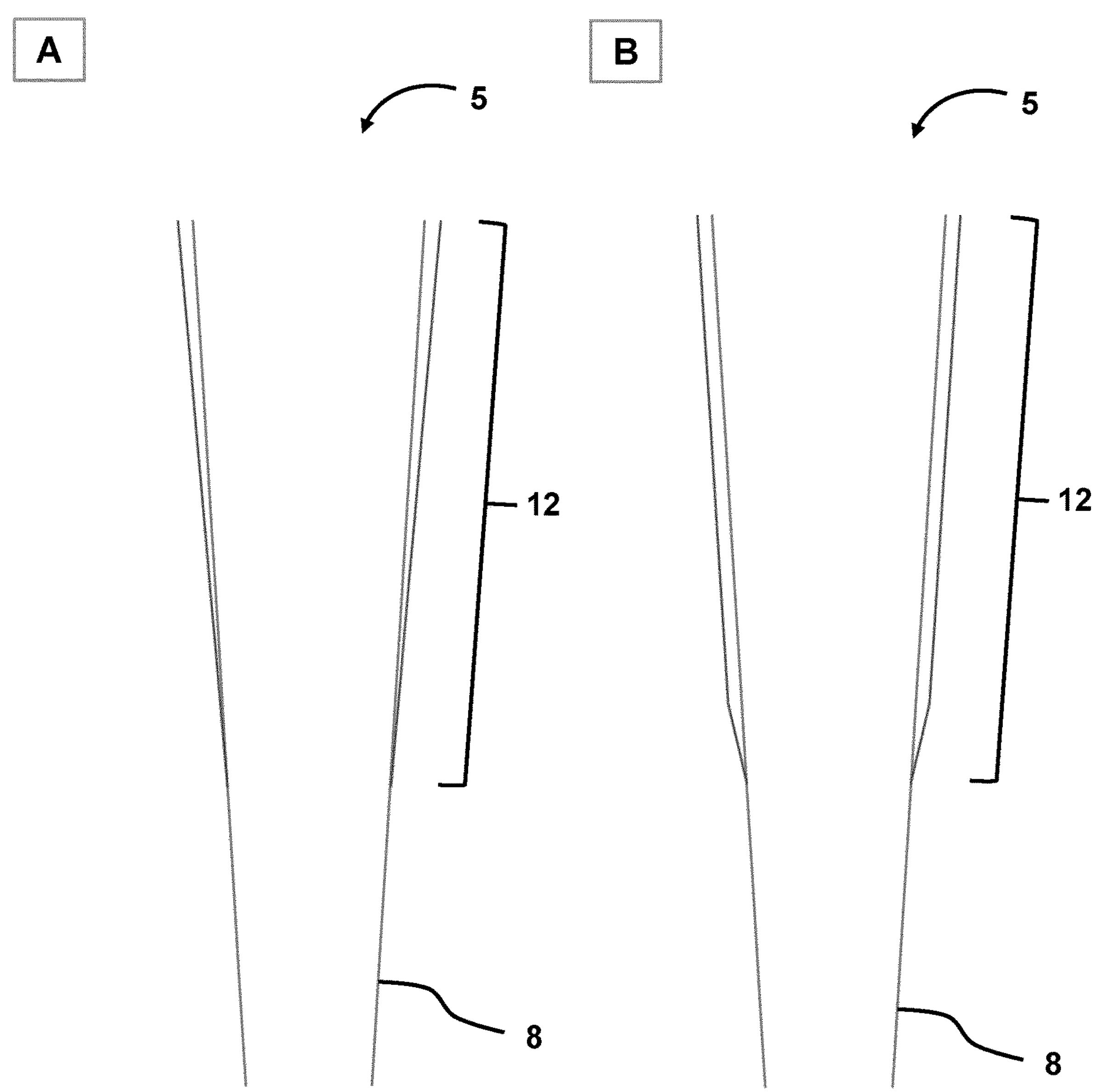

FIGS. 9A and 9B depicts profiles of the stem according to embodiments of the invention, in which FIGS. 9A and 9B are showing different profiles.

Figure 10:
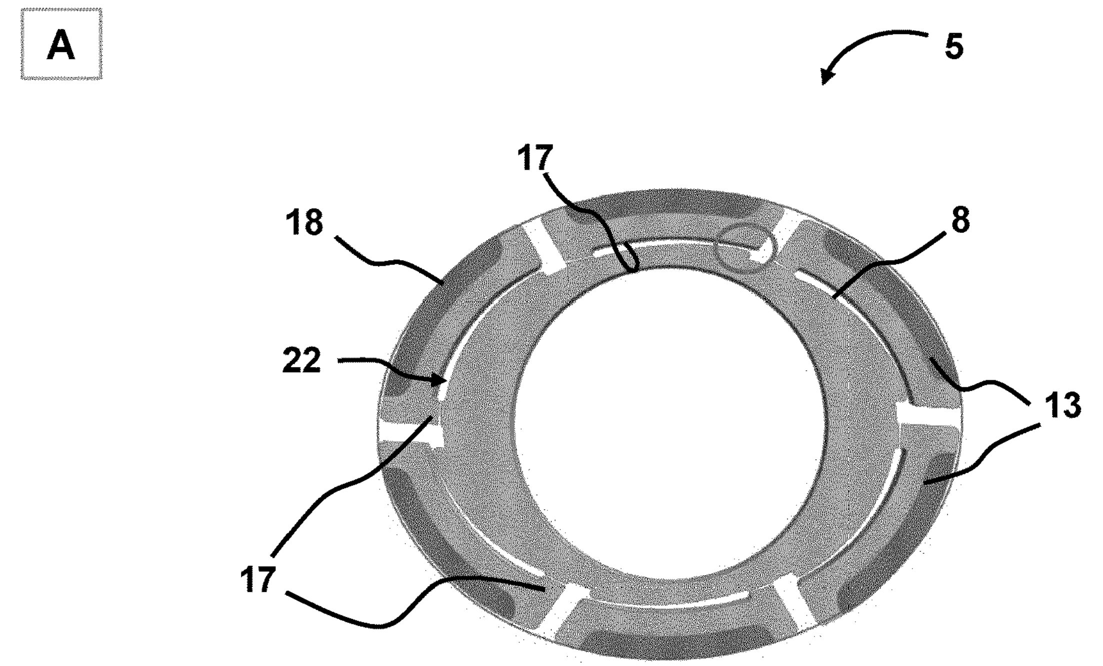

FIGS. 10A and 10B show the stem according to embodiments of the invention, in which the outer shape of the stem is compressed towards the external surface of the stem. FIG. 10A shows a cut-away view from the proximal end of the stem at 50% lamella compression, and FIG. 10B shows a cut-away view from the proximal end of the stem at 100% lamella compression.

Figure 11:
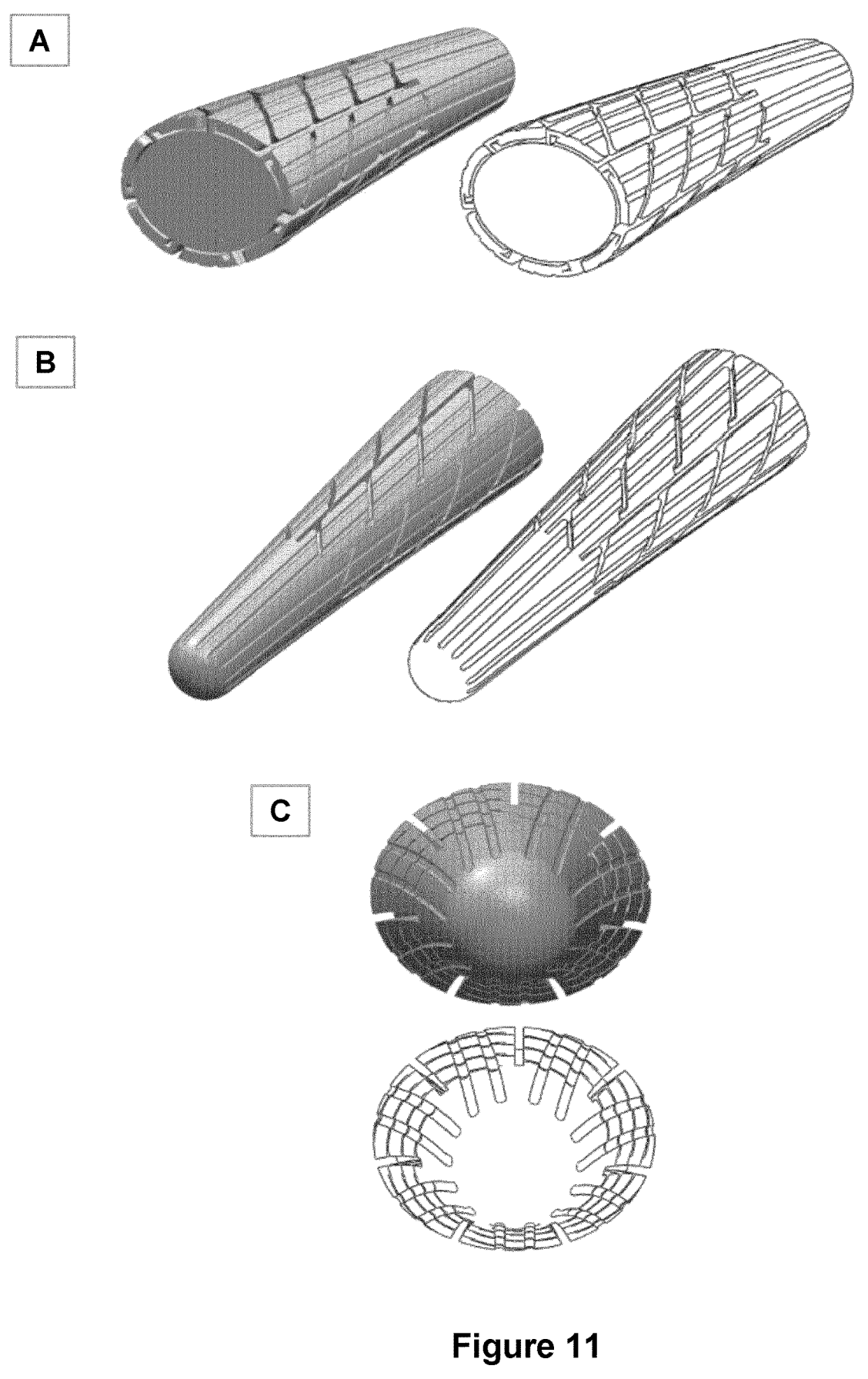

FIGS. 11A, 11B, and 11C show the stem according to embodiments of the invention, in which the stem includes longitudinal ridges and/or grooves. FIG. 11A shows a perspective view from the proximal end of the stem, FIG. 11B shows a perspective view from the distal end of the stem, and FIG. 11C shows another view from the distal end of the stem.

Figure 12:
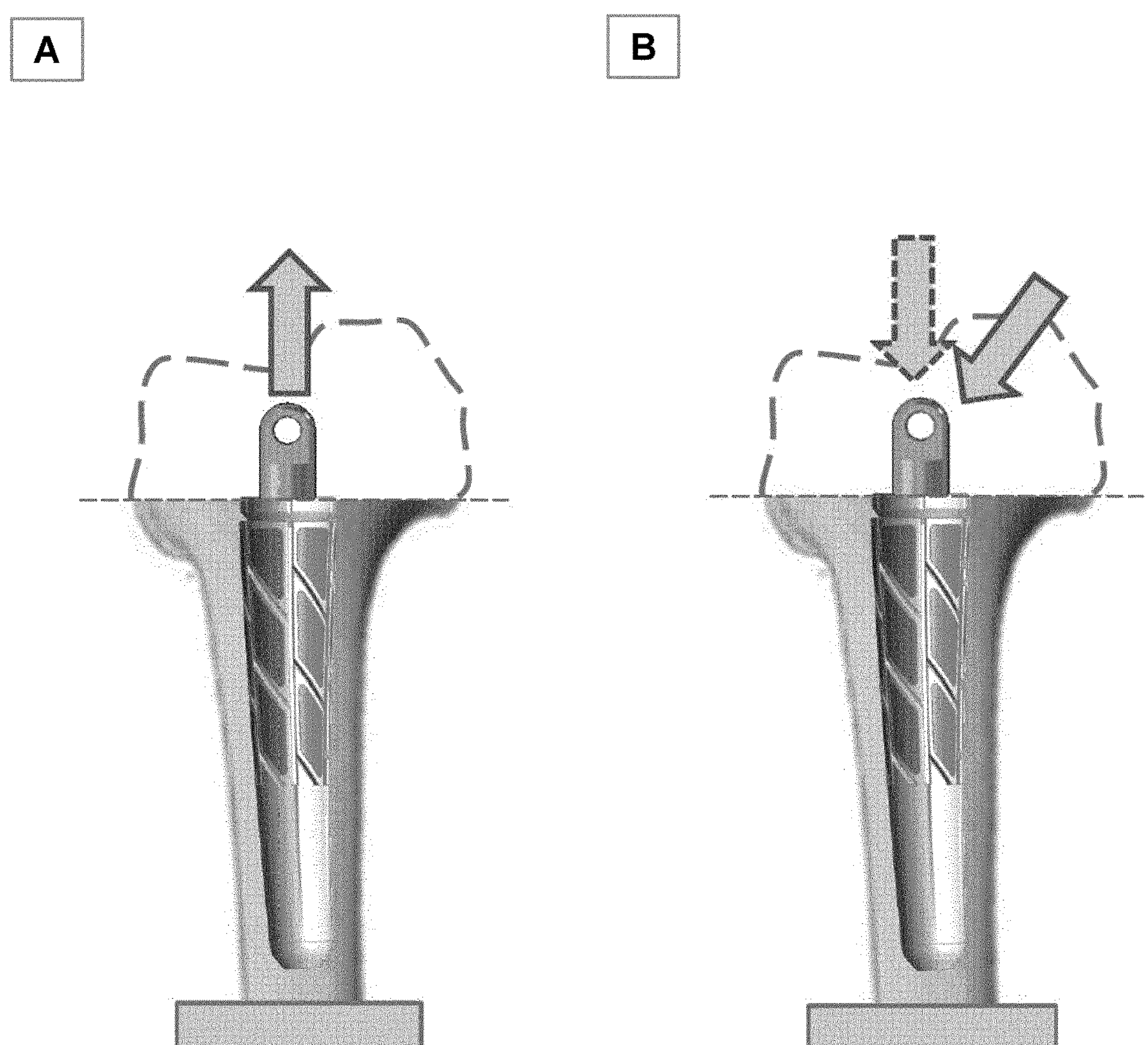

FIGS. 12A and 12B show a testing set-up the stem according to embodiments of the invention, as described in the Example. FIG. 12A shows a view of a stem implanted into bone and undergoing a static push force, and FIG. 12B shows a view of a stem implanted into bone and undergoing dynamic micromovement forces.

DETAILED DESCRIPTION OF THE INVENTION

The present invention relates to a prosthesis or implant device for use in joint or bone repair or restoration of function, in which the prosthesis or implant device comprises a stem having an exterior surface that is flexible and can circumferentially compress when implanted into bone. By having such flexibility, there is a lower risk of damage to the surrounding bone, as well as lower sensitivity to the effects of an imperfect position of the stem within the bone. In addition, the flexibility of the stem reduces the difference in stiffness between the prosthesis or implant device and the surrounding bone, which provides the prosthesis or implant device with a more stable fit in the bone.

Prosthesis/Implant Device of the Invention

Figure 1:
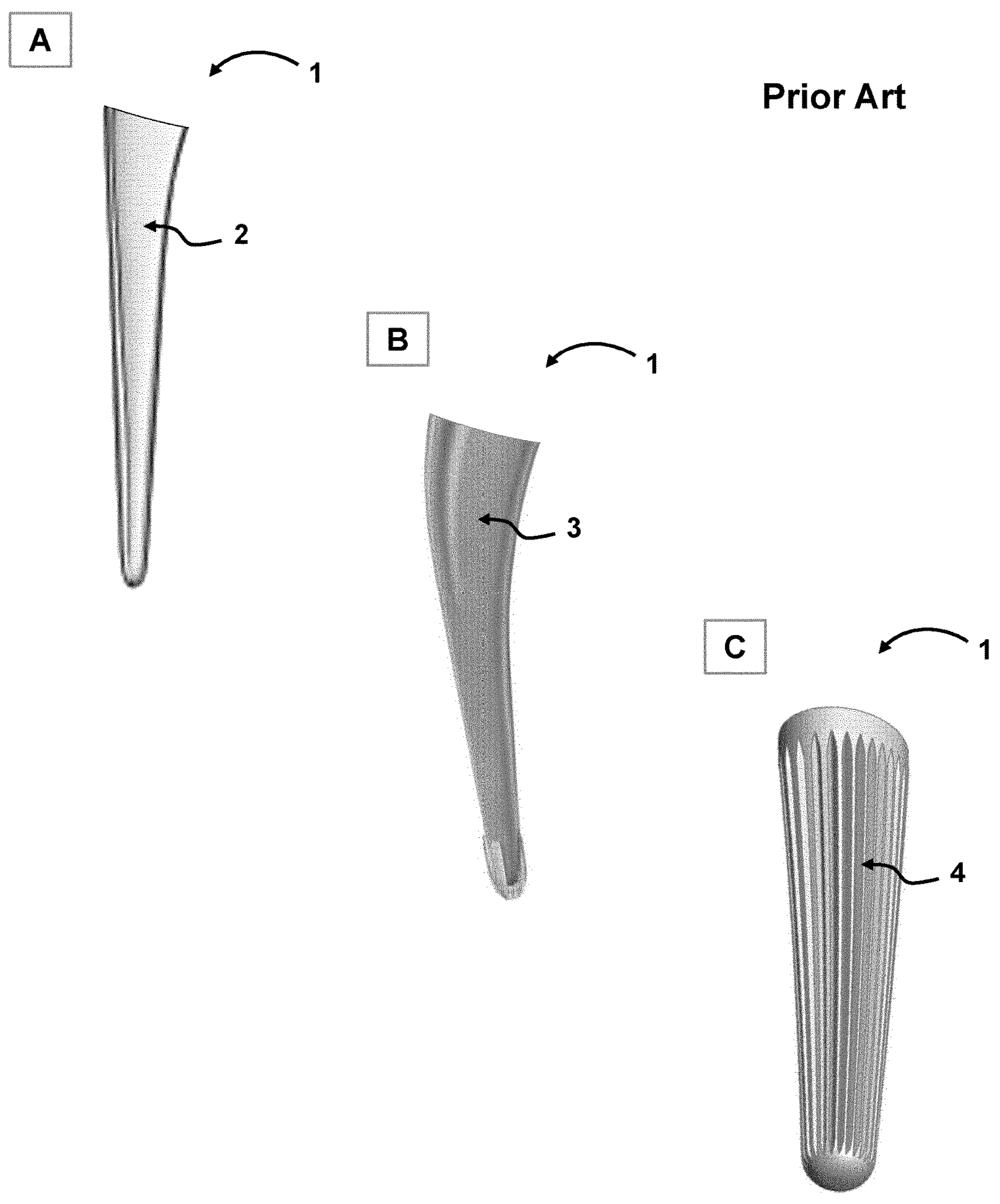
FIGS. 1A-1C show prosthetic stem surface designs known in the art.
Figure 2:
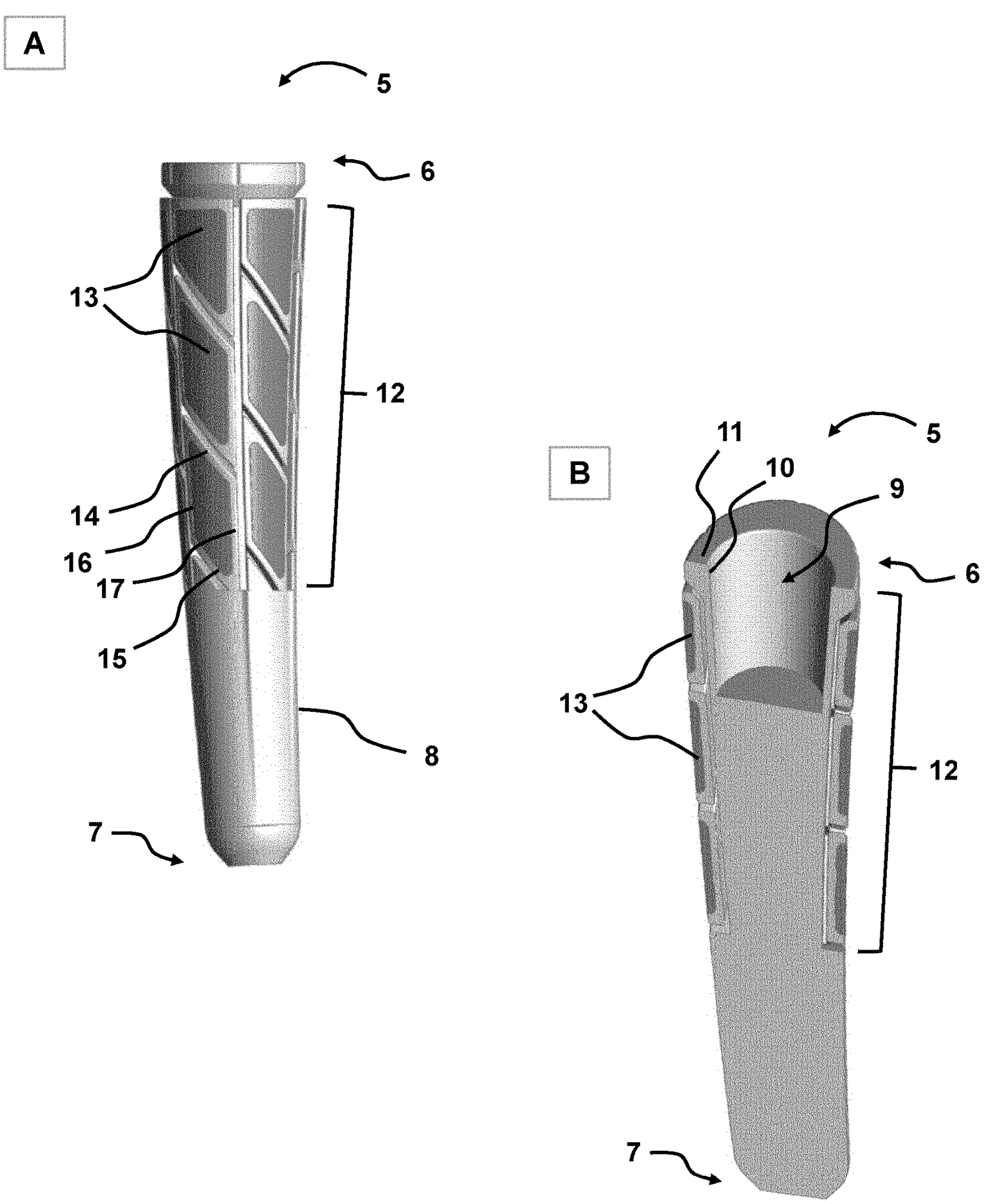
FIGS. 2A and 2B show the stem according to embodiments of the invention.
Figure 3:
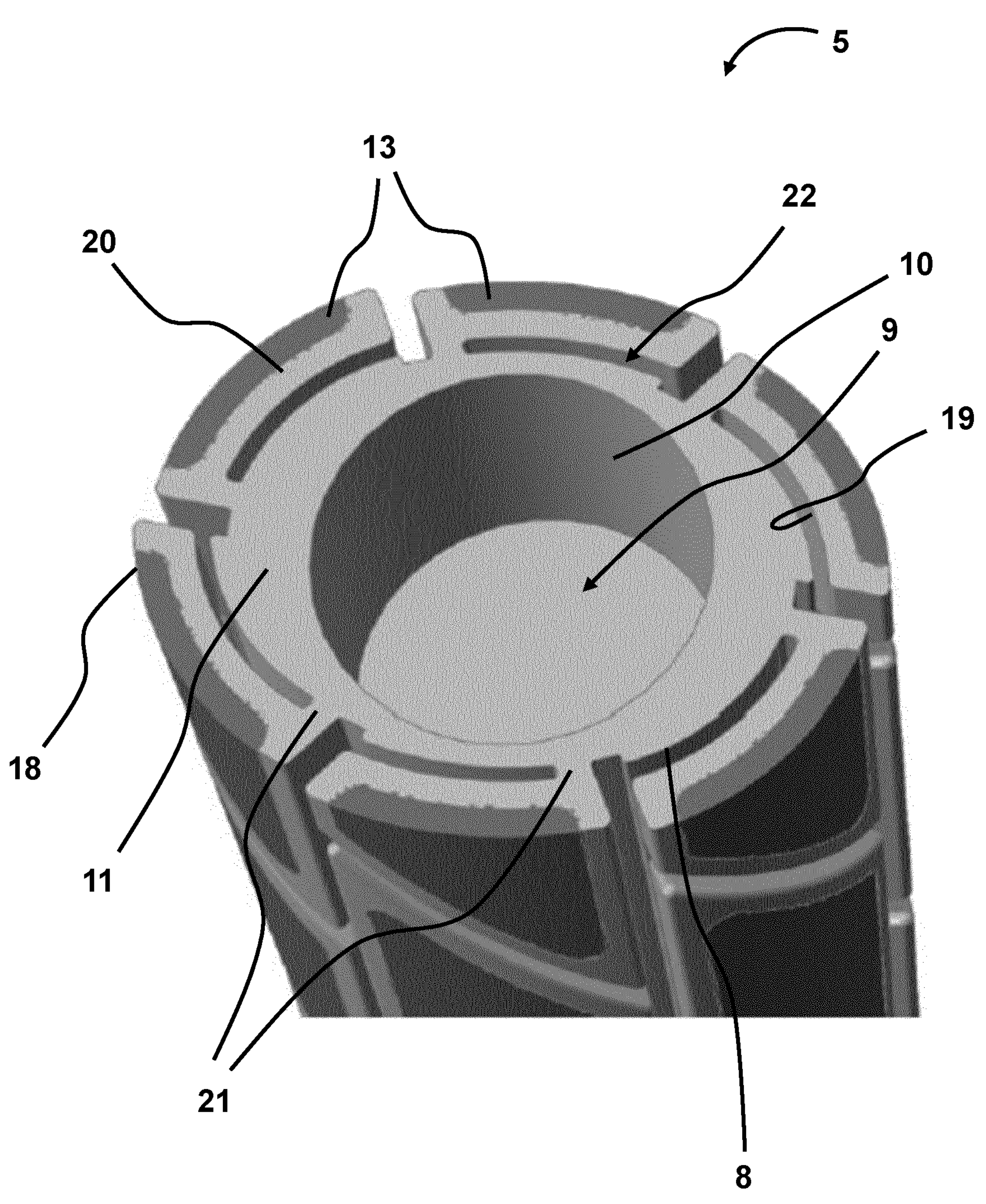
FIG. 3 shows a perspective cut-away view of the proximal end of the stem according to embodiments of the invention.

The prosthesis or implant device of the invention comprises a stem. As shown in FIGS. 2A-3, the stem 5 comprises a proximal end 6, a distal end 7 opposite the proximal end 6, and an external surface 8. As used herein, the terms "proximal" and "distal" is relative to how the stem 5 is inserted into the bone upon implantation, such that the stem 5 is inserted in the direction of the distal end 7.

In some embodiments, the stem 5 may comprise substantially the shape of a circular cylinder or an elliptical cylinder. In certain embodiments, the stem 5 may comprise substantially the shape of a circular cylinder or an elliptical cylinder that tapers towards the distal end 7, such that the cross-sectional area at the proximal end 6 is greater than the cross-section area at the distal end 7. Hence, in certain embodiments, the stem 5 may comprise substantially the shape of a circular cone or portion thereof, or substantially the shape of an elliptical cone or portion thereof; or the stem 5 may comprise substantially the shape of a rounded circular cone or portion thereof, or a rounded elliptical cone or portion thereof, in which the distal end 7 is a rounded vertex, rather than a point.

In certain embodiments, the stem 5 may comprise a curvature from the proximal end 6 to the distal end 7. Such a curvature may accommodate the natural curvature of the bone into which the stem 5 is being implanted, e.g., the curvature of the femur, tibia, humerus, etc.

The stem 5 may comprise a channel 9 that extends at least partially through the stem 5 from the proximal end 6 towards the distal end 7. In such embodiments in which a channel 9 is present, the stem 5 further comprises an internal surface 10 that defines the channel 9, and a thickness 11 between the external surface 8 and the internal surface 10.

A section 12 of the stem 5 may comprise two or more non-overlapping lamellas 13 around part or all of the circumference of the stem 5. In some embodiments, the lamellas 13 may be arranged in two or more columns of lamellas 13 in the direction of the proximal end 6 to the distal end 7, and two or more rows of lamellas 13 around the circumference of the stem, as shown in FIG. 2A.

Figure 4:
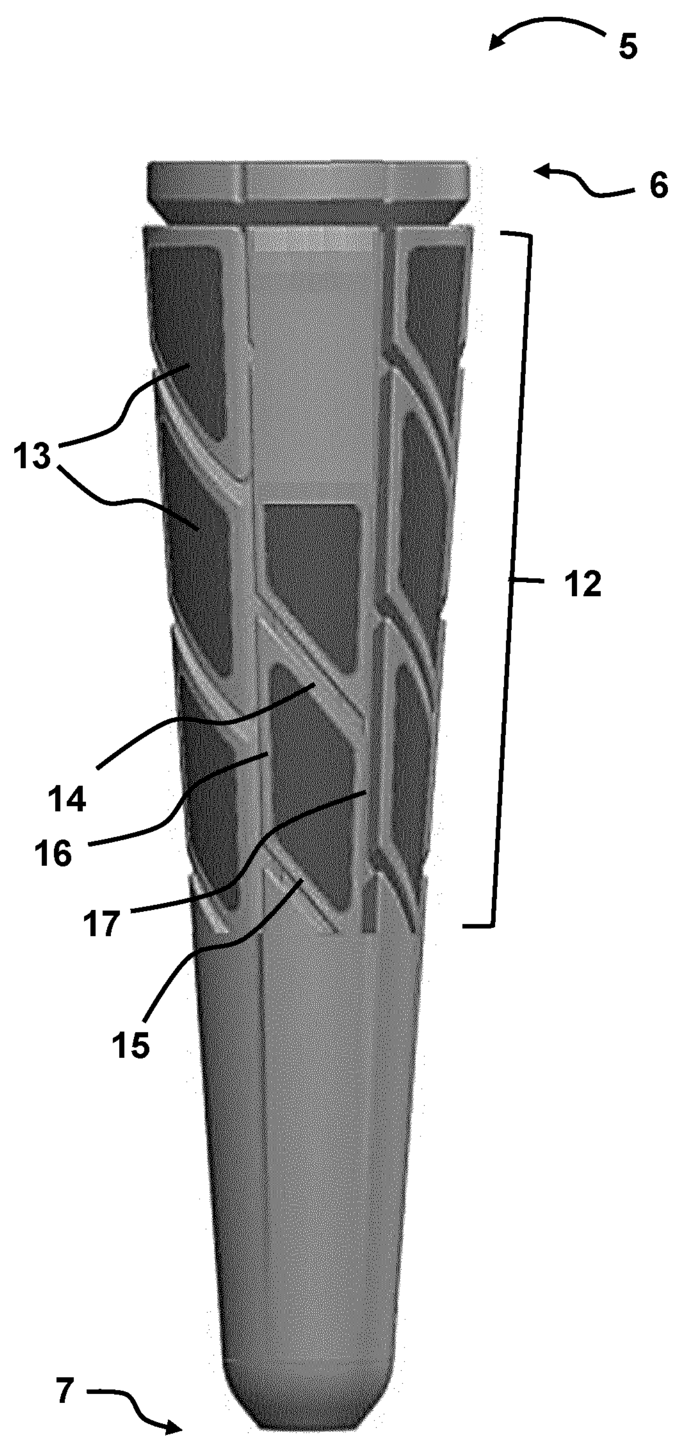
FIG. 4 shows a view of the stem according to embodiments of the invention, in which the number of lamellas in the columns are not all the same.

In some embodiments, the number of lamellas 13 in each column is the same. In certain embodiments, one or more columns of lamellas 13 may comprise one or more fewer lamellas 13, such as a lamella 13 that is not present in the row adjacent to the proximal end 6 (for example, see FIG. 4), or a lamella 13 not present in the row closest to the distal end 7 (not shown).

Each lamella 13 may comprise generally any enclosed shape, such as a polygon. In some embodiments, each lamella 13 may substantially comprise a shape of a quadrilateral, preferably a trapezoid or a parallelogram, such as a non-rectangular parallelogram, a rhombus, a rectangle, or a square. In preferred embodiments, each lamella 13 may substantially comprise the shape of a trapezoid.

In embodiments in which each lamella 13 substantially comprises a shape of a quadrilateral, the lamella 13 may comprise a proximal edge 14, a distal edge 15, a left edge 16, and a right edge 17. These terms are based on the stem 5 being in an orientation such that the proximal end 6 is above and the distal end 7 is below, for example, the orientation shown in FIGS. 2A and 2B. The proximal edge 14 is the edge nearest the proximal end 6, and the distal edge 15 is the edge nearest the distal end 7. In some embodiments, the proximal edge 14 and the distal edge 15 are parallel. In some embodiments, the proximal edge 14 and the distal edge 15 are not parallel.

The left edge 16 and the right edge 17 extend between the proximal edge 13 and the distal edge 14. In some embodiments in which the stem 5 comprise substantially the shape of a circular cylinder or an elliptical cylinder, the proximal edge 13 and the distal edge 14 may be parallel. In some embodiments in which the stem 5 comprise substantially the shape of a circular cone or portion thereof, or an elliptical cone or portion thereof, or a rounded circular cone or portion thereof, or a rounded elliptical cone or portion thereof, the proximal edge 14 and the distal edge 15 may not be parallel.

In some embodiments, the lamellas 13 may comprise different shapes. For instance, the first row of lamellas, i.e., the row of lamellas closest to the proximal end 6, may substantially comprise a quadrilateral shape in which the proximal edge 14 and the distal edge 15 are not parallel, and the second row of lamellas may substantially comprise a quadrilateral shape in which the proximal edge 14 and the distal edge 15 are parallel.

Each lamella 13 may also comprise an outer surface 18, an inner surface 19, and a thickness 20 between the outer surface 18 and the inner surface 19. The lamella 13 may be connected to the external surface 8 of the stem 5 by a bending joint 21 at or adjacent to one or more of the edges (e.g., the proximal edge 14, distal edge 15, left edge 16, and/or right edge 17) on the inner surface 19 of the lamella 13; the rest of the inner surface 19 of the lamella 13 is separated from the external surface 8 of the stem 5 by a space 22. In certain embodiments, the lamella 13 is connected to the external surface 8 of the stem 5 by a bending joint 21 at or adjacent to one or two of the edges, preferably one of the edges.

Figure 5:
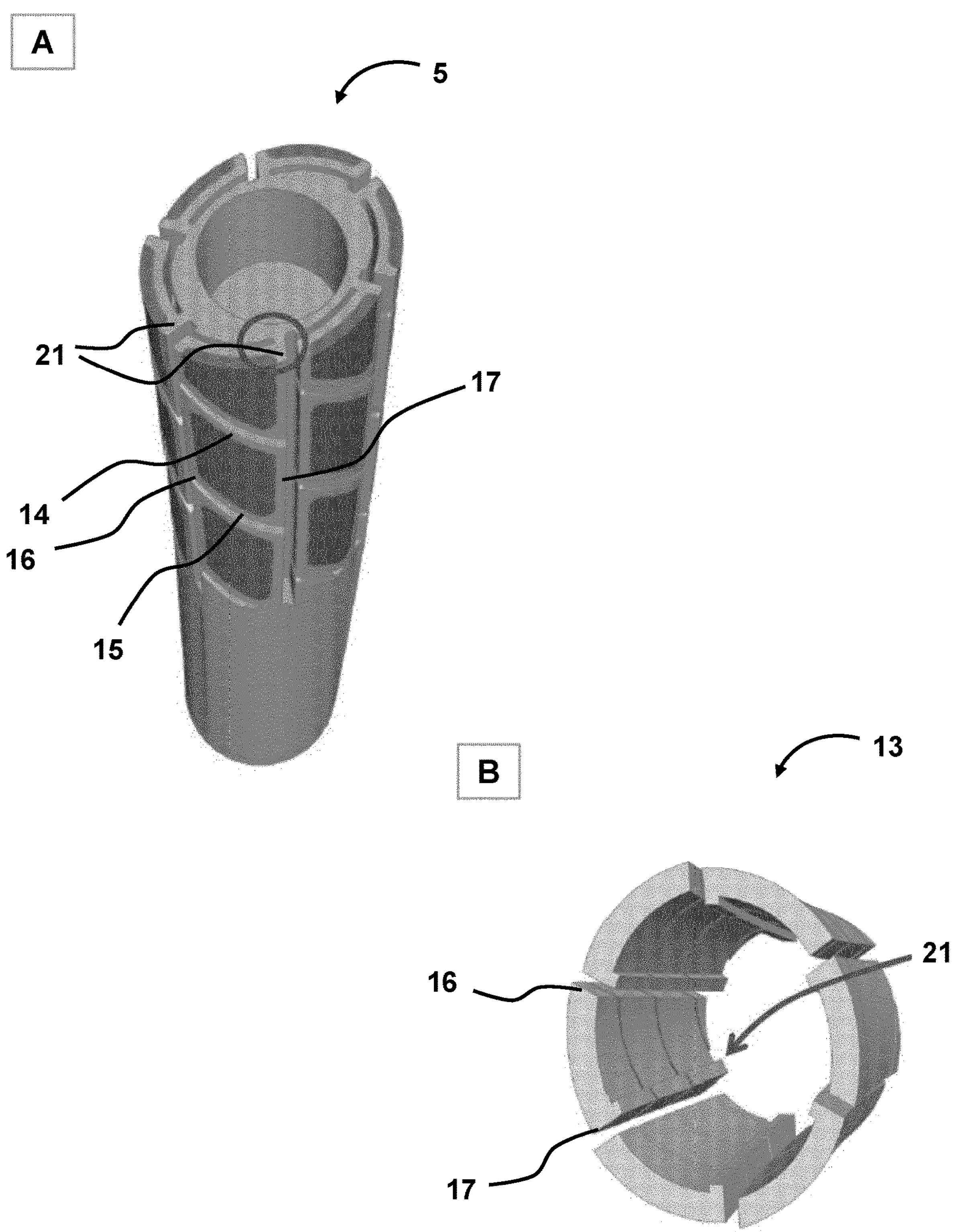
FIGS. 5A and 5B show the stem or aspects thereof according to embodiments of the invention, in which the bending joint is on the right edge of the lamellas.
Figure 6:
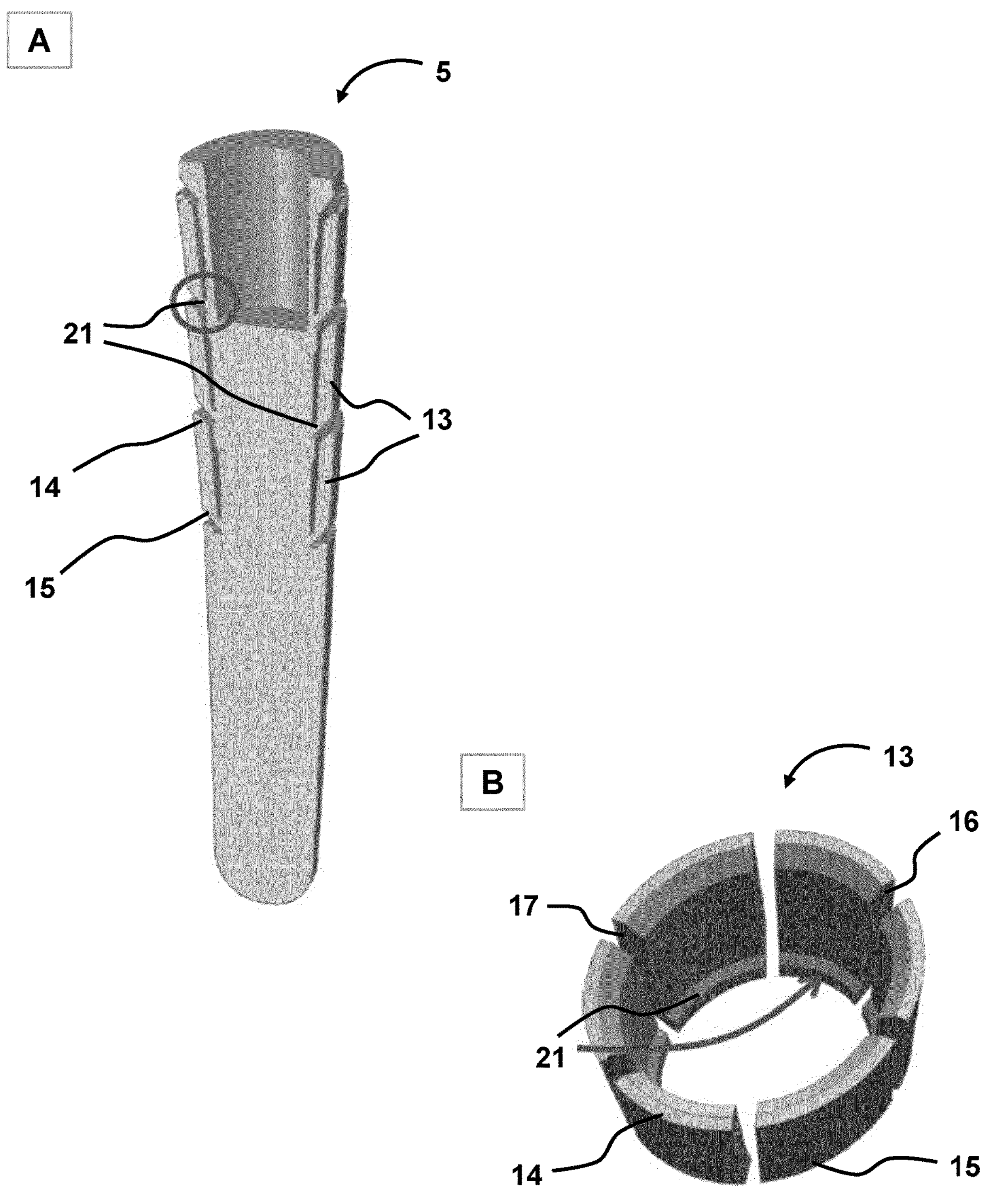
FIGS. 6A and 6B show the stem or aspects thereof according to embodiments of the invention, in which the bending joint is on the distal edge of the lamellas.

In some embodiments, the bending joint 21 is located along the right edge 17 of the lamellas 13, as shown in FIGS. 5A and 5B. In some embodiments, the bending joint 21 is located along the left edge 16 of the lamellas 13 (not shown). Alternatively, the bending joint 21 is located along the distal edge 15, as shown in FIGS. 6A and 6B. Or, the bending joint 21 may be located along the proximal edge 14 (not shown).

The bending joint 21 is flexible, such that an application of force to the outer surface 18 of the lamella 13, for example when the stem 5 is press-fitted into a volume (e.g., a bore) in bone, can cause the lamella 13 to move towards the external surface 8 of the stem 5 and reduce the space 22.

The bending joint 21 may extend along a portion of the edge of the lamella 13, or along the entire edge of the lamella 13. The bending joint 21 may comprise a single continuous connection point 23 between the lamella 13 and the external surface 8 of the stem 5 (see FIG. 7A). Alternatively, the bending joint 21 may comprise more than one connection point 23 between the lamella 13 and the external surface 8 of the stem 5, such that there are discontinued portions (e.g., spaces) 24 of the bending joint 21 in which the lamella 13 and the external surface 8 of the stem 5 are not connected (see FIG. 7B). The width of these disconnected portions 24 may vary, ranging from about 2 mm to about 10 mm, or about 4 mm to about 8 mm. In certain embodiments, these discontinued portions 24 may extend into the thickness 20 of the lamella 13 as shown in FIG. 7C, for example, by a distance ranging from about 0.5 mm to about 5 mm, or about 1 mm to about 3 mm.

In some embodiments, the outer surface 18 of the lamellas 13 may comprise a surface feature 25 to promote bone growth against and/or into the lamellas 13 (see FIG. 8A). The surface feature 25 may be across the entire outer surface 18 of the lamella 13 or a portion thereof. Examples of a surface feature 25 may include, but are not limited a texture, porous coating, bioactive coating, or a combination thereof. In some embodiments, the surface feature 25 may be a porous structure as described in U.S. Patent Publication No. 2018/0193152, which is incorporated herein by reference. In certain embodiments, the surface feature 25 comprises the TrabecuLink® structure.

In other embodiments, the outer surface 18 of the lamellas 13 does not comprise a surface feature 25 (see FIG. 8B).

In some embodiments, the profile of the stem 5 in section 12 may be greater than the rest of the stem 5 due to the presence of the lamellas 13, as shown in FIGS. 9A and 9B. The profile of the stem 5 in section 12 may gradually increase towards the proximal end 6 of the stem 5 as shown in FIG. 5A, or may more distinctly increase as shown in FIG. 5B. If the section 12 overlaps with the location of the channel 9 in the stem 5, the thickness 11 between the external surface 8 of the stem 5 and the internal surface 10 of the channel 9 may be reduced to partially accommodate the lamellas 13. In some embodiments, the profile of the stem 5 may be compressed, such that the lamella 13 is close to the external surface 8 of the stem 5 and the space 22 is reduced. The degree of compression may range from about 50%, in which there remains a distance between the inner surface 19 of the lamella 13 and the external surface 8 of the stem 5 (see FIG. 10A), to about 100%, in which a portion of the inner surface 19 of the lamella 13 contacts the external surface 8 of the stem 5 (see FIG. 10B).

In some embodiments, the outer surface 18 of the lamella 13 and the external surface 8 of the stem 5 include longitudinal ridges and/or grooves, as shown in FIGS. 11A, 11B, and 11C. In this regard, the longitudinal ridges and/or grooves can extend continuously from the proximal end 6 to the distal end 7. The ridges and/or grooves can improve the intermedullary gliding of the stem 5 in both longitudinal directions, thereby allowing for an easier introduction and removal of the stem 5.

The stem may be comprised of materials known in the field for orthopedic prostheses or implants. For example, the stem may comprise titanium, cobalt chromium, or medical grade stainless steel. In some embodiments, the stem comprises commercially pure titanium (CP-Ti) or a titanium alloy (e.g., Ti-6Al-4V or Ti-4Al-4V). In some embodiments, the stem comprises cobalt chrome molybdenum (Co—Cr—Mo). In preferred embodiments, the stem, including the lamellas and the bending joints, are comprised of the same material. In certain embodiments, the lamellas and/or the bending joints are comprised of a different material than the rest of the stem and/or than each other.

The prosthesis or implant device of the invention may be manufactured by methods known in the art. In particular embodiments, the prosthesis or implant device of the present invention may be fabricated by additive manufacturing technologies including, but not limited to, electron beam melting (EBM) and selective laser melting (SLM). In alternative embodiments, the prosthesis or implant device can be manufactured by conventional means such as precision casting.

The prosthesis of the present invention may be for use in replacement or repair of any joint requiring a prosthesis that includes a stem. In some embodiments, the prosthesis may be a knee replacement prosthesis in which the stem is part of the tibia component or the femoral component. In some embodiments, the prosthesis may be a hip replacement prosthesis in which the stem is part of the femoral component. In some embodiments, the prosthesis may be a shoulder replacement prosthesis, in which the stem is part of the humeral component.

In other embodiments, the present invention relates to a hip replacement prosthesis in which the acetabular component comprises at least two non-overlapping lamellas on the outside surface of the acetabular component (i.e., the surface that faces the acetabulum of the hip), the inside surface of the acetabular component (i.e., the surface that faces the head of the femoral component), or both. In some embodiments, the acetabular component may be used in combination with the femoral component that comprises a stem according to the present invention.

In some embodiments, the implant device of the present invention may be an intramedullary nail comprising a shaft, in which a portion of the shaft comprises at least two non-overlapping lamellas as described above. Accordingly, an aspect of the present invention relates to an intramedullary nail. In some embodiments, the shaft of the intramedullary nail may comprise any combination of features that is described herein for the stem.

In further embodiments, the implant device is a dental implant comprising a stem of the present invention. Accordingly, an aspect of the present invention relates to a dental implant. In some embodiments, one or more lamellas of the stem may comprise further geometries on their outer surface, for example, threaded circumferential elevation to ease implantation and/or to stabilize the implant upon implantation (e.g., increase implant pull-out resistance).

Uses of the Invention

An aspect of the present invention is directed to (i) a method of treating a subject in need of joint replacement; (ii) use of the prosthesis of the present invention for treating a subject in need of joint replacement; and (iii) the prosthesis of the present invention for use in treating a subject in need of joint replacement. In some embodiments, the subject is in need of replacement of the knee, hip, or shoulder.

An aspect of the present invention is directed to (i) a method of treating a subject in need of bone repair; (ii) use of the prosthesis of the present invention for treating a subject in need of bone repair; and (iii) the prosthesis of the present invention for use in treating a subject in need of bone repair. In some embodiments, the bone repair may be due to a break or fracture in the bone.

Another aspect of the present invention is directed to (i) a method of reducing risk of bone damage caused by implantation of a prosthesis in a subject; (ii) use of the prosthesis of the present invention for reducing risk of bone damage caused by implantation of a prosthesis in a subject; and (iii) the prosthesis of the present invention for use in reducing risk of bone damage caused by implantation of a prosthesis in a subject.

A further aspect of the invention is directed to (i) a method of reducing incidence of bone damage caused by implantation of a prosthesis in a subject; (ii) use of the prosthesis of the present invention for reducing incidence of bone damage caused by implantation of a prosthesis in a subject; and (iii) the prosthesis of the present invention for use in reducing incidence of bone damage caused by implantation of a prosthesis in a subject.

An aspect of the invention is directed to (i) method of reducing incidence of aseptic implant loosening in a subject; (ii) use of the prosthesis of the present invention for reducing incidence of aseptic implant loosening in a subject; and (iii) the prosthesis of the present invention for use in reducing incidence of aseptic implant loosening in a subject.

These methods or uses of the present invention may comprise implanting the prosthesis of the present invention in the subject. Implantation of the prosthesis may comprise (a) preparing a bore in the bone in which the prosthesis is to be implanted; and (b) implanting the prosthesis in which the stem of the prosthesis or a portion thereof is press-fitted into the bore.

An aspect of the present invention is directed to (i) a method of treating a subject in need of bone repair; (ii) use of the intramedullary nail of the present invention for treating a subject in need of bone repair; and (iii) the intramedullary nail of the present invention for use in treating a subject in need of bone repair. In some embodiments, the bone repair may be due to a break or fracture in the bone.

Another aspect of the present invention is directed to (i) a method of reducing risk of bone damage caused by implantation of an intramedullary nail in a subject; (ii) use of the intramedullary nail of the present invention for reducing risk of bone damage caused by implantation of an intramedullary nail in a subject; and (iii) the intramedullary nail of the present invention for use in reducing risk of bone damage caused by implantation of an intramedullary nail in a subject.

A further aspect of the invention is directed to (i) a method of reducing incidence of bone damage caused by implantation of an intramedullary nail in a subject; (ii) use of the intramedullary nail of the present invention for reducing incidence of bone damage caused by implantation of an intramedullary nail in a subject; and (iii) the intramedullary nail of the present invention for use in reducing incidence of bone damage caused by implantation of an intramedullary nail in a subject.

These methods or uses of the present invention may comprise implanting the intramedullary nail of the present invention in the subject. Implantation of the intramedullary nail may comprise inserting the intramedullary nail into the bone in need of repair or treatment. In some embodiments, implantation may comprise (a) preparing a bore in the bone in which the intramedullary nail is to be implanted; and (b) implanting the intramedullary nail in which the shaft of the prosthesis or a portion thereof is press-fitted into the bore.

An aspect of the present invention is directed to (i) a method of treating a subject in need of dental repair or restoration of function; (ii) use of the dental implant of the present invention for treating a subject in need of dental repair or restoration of function; and (iii) the dental implant of the present invention for use in treating a subject in need of dental repair or restoration of function. The dental implant may support a dental prosthesis such as a crown, bridge, denture, or facial prosthesis, or to act as an orthodontic anchor.

This method or uses of the present invention may comprise implanting the dental implant of the present invention in the subject. Implantation of the dental implant may comprise inserting the dental implant into the jawbone. In some embodiments, implantation may comprise (a) preparing a bore in the bone in which the dental implant is to be implanted; and (b) implanting the dental implant in which the implant or a portion thereof is press-fitted into the bore.

A "subject" as used herein refers to any "individual" or "animal" or "patient" or "mammal" for whom these methods and uses of the invention are desired. Mammalian subjects include humans, domestic animals, farm animals, sports animals, and laboratory animals including, e.g., humans, non-human primates, canines, felines, porcines, bovines, equines, rodents, including rats and mice, rabbits, etc.

EXAMPLES

Example 1

The stem of the prostheses of the invention is tested for adherence to the bone after implantation. For instance, the stem is implanted into the tibia of one or more subjects, such as canines or porcines. After sufficient time passes to allow the stem to adhere, the tibia is harvested from each subject and is subjected to either a static force (see FIG. 12A) or dynamic micromovements (see FIG. 12B) to determine the extent adherence of the stem to the bone.

The foregoing description is given for clearness of understanding only, and no unnecessary limitations should be understood therefrom, as modifications within the scope of the invention may be apparent to those having ordinary skill in the art.

Detailed embodiments of the present prostheses and implant devices and methods are disclosed herein; however, it is to be understood that the disclosed embodiments are merely illustrative and that the prostheses and implant devices and methods may be embodied in various forms. In addition, each of the examples given in connection with the various embodiments of the systems and methods are intended to be illustrative, and not restrictive.

Throughout this specification and the claims which follow, unless the context requires otherwise, the word "comprise" and variations such as "comprises" and "comprising" will be understood to imply the inclusion of a stated integer or step or group of integers or steps but not the exclusion of any other integer or step or group of integers or steps.

Throughout the specification, where compositions are described as including components or materials, it is contemplated that the compositions can also consist essentially of, or consist of, any combination of the recited components or materials, unless described otherwise. Likewise, where methods are described as including particular steps, it is contemplated that the methods can also consist essentially of, or consist of, any combination of the recited steps, unless described otherwise. The invention illustratively disclosed herein suitably may be practiced in the absence of any element or step which is not specifically disclosed herein.

The practice of a method disclosed herein, and individual steps thereof, can be performed manually and/or with the aid of or automation provided by electronic equipment. Although processes have been described with reference to particular embodiments, a person of ordinary skill in the art will readily appreciate that other ways of performing the acts associated with the methods may be used. For example, the order of various steps may be changed without departing from the scope or spirit of the method, unless described otherwise. In addition, some of the individual steps can be combined, omitted, or further subdivided into additional steps.

All patents, publications and references cited herein are hereby fully incorporated by reference. In case of conflict between the present disclosure and incorporated patents, publications and references, the present disclosure should control.

What is claimed is:

1. An implant for use in joint or bone repair comprising a stem having a proximal end, a distal end, and an external surface, in which a portion of the stem comprises two or more non-overlapping lamellas around part or all of the circumference of the stem; wherein:

each lamella comprises an outer surface, an inner surface, and a thickness therebetween, wherein the inner surface of the lamella faces the external surface of the stem, each lamella is connected to the external surface of the stem via a bending joint on the inner surface of the lamella, wherein each of the lamellas comprises a proximal edge, a distal edge, a left edge, and a right edge, wherein the proximal edge is the edge nearest the proximal end, and the distal edge is the edge nearest the distal end, wherein the bending joint is on either the right edge of the lamella between the proximal edge and the distal edge, or on the left edge of the lamella between the proximal edge and the distal edge, and wherein the rest of the inner surface of the lamella and the external surface of the stem is separated by a space;

the bending joint permits the space between the rest of the inner surface of the lamella and the external surface of the stem to decrease upon application of a force to the outer surface of the lamella, wherein the lamellas are arranged in two or more columns of lamellas in a direction of the proximal end to the distal end of the stem, and two or more rows of lamellas around the circumference of the stem, and when implanted in a body, the space between the inner surface of the lamella and the external surface of the stem can decrease but cannot increase.

2. The implant of claim 1, wherein the stem comprises substantially a shape of a cylinder, and, wherein the cylinder is a circular cylinder or an elliptical cylinder.

3. The implant of claim 1, wherein the stem comprises a taper between the proximal end and the distal end.

4. The implant of claim 3, wherein the stem comprises substantially a shape of a rounded cone or portion thereof, wherein the rounded cone is a rounded circular cone or a rounded elliptical cone.

5. The implant of claim 1, wherein the number of lamellas in each column and each row is not the same.

6. The implant of claim 1, wherein each of the lamellas comprises substantially a shape of a trapezoid.

7. The implant of claim 1, wherein the bending joint provides on the edge of the lamella, or adjacent thereto, two or more connection points between the inner surface of the lamella and the external surface of the stem.

8. The implant of claim 1, wherein the implant is one of the following: a prosthesis, a dental implant, or an intramedullary nail.

9. A method of treating a subject in need of dental repair, the method comprising implanting into the subject the dental implant of claim 8.

10. The implant of claim 1, wherein the bending joint provides on the edge of the lamella, or adjacent thereto, two connection points between the inner surface of the lamella and the external surface of the stem, wherein there is a discontinued portion of the bending joint between the two connection points in which the lamella and the external surface of the stem are not connected.

11. The implant of claim 1, wherein the portion of the stem comprises two or more non-overlapping lamellas around all of the circumference of the stem.

12. The implant of claim 1, wherein each of the lamellas comprises substantially a shape of a trapezoid or parallelogram.

13. The implant of claim 1, wherein the bending joint provides on the edge of the lamella, or adjacent thereto, two connection points between the inner surface of the lamella and the external surface of the stem, wherein there is a discontinued portion of the bending joint between the two connection points in which the lamella and the external surface of the stem are not connected, and wherein the discontinued portion extends into a thickness of the lamella.

14. The implant of claim 1, wherein the proximal edge and the distal edge are free from connection to the external surface of the stem.

15. The implant of claim 1, wherein the lamella is configured to flex about the bending joint in a circumferential direction around the stem.

16. The implant of claim 1, wherein the outer surface of the lamella and the external surface of the stem include longitudinal ridges and grooves that extend continuously from the proximal end to the distal end.

17. The implant of claim 1, wherein the stem comprises a curvature from the proximal end to the distal end to accommodate a natural curvature of bone into which the stem is being implanted.

18. A method of treating a subject in need of joint replacement or bone repair, the method comprising implanting into the subject the implant of claim 1.

19. A method of reducing risk and incidence of bone damage caused by implantation of an implant in a subject, the method comprising implanting into the subject the implant of claim 1.

20. A method of reducing incidence of aseptic implant loosening in a subject, the method comprising implanting into the subject the implant of claim 1.

* * * * *